United States Patent
Lu et al.

(10) Patent No.: US 10,538,545 B2
(45) Date of Patent: Jan. 21, 2020

(54) DINITROSYL IRON COMPLEX, PHARMACEUTICAL COMPOSITION COMPRISING THE SAME, COMPOSITE MATERIAL COMPRISING THE SAME, AND USES THEREOF

(71) Applicant: Chung Yuan Christian University, Taoyuan (TW)

(72) Inventors: Tsai-Te Lu, Taoyuan (TW); Hsiao-Wen Huang, Taoyuan (TW); Chia-Her Lin, Taoyuan (TW); Yu-Ting Tseng, Taoyuan (TW); Wen-Feng Liaw, Taoyuan (TW); Hsi-Ya Huang, Taoyuan (TW); Show-Jen Chiou, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 8 days.

(21) Appl. No.: 15/413,428

(22) Filed: Jan. 24, 2017

(65) Prior Publication Data
US 2018/0208616 A1    Jul. 26, 2018

(51) Int. Cl.
*C07F 15/02*    (2006.01)
*A61K 31/555*   (2006.01)

(52) U.S. Cl.
CPC .......... *C07F 15/025* (2013.01); *A61K 31/555* (2013.01)

(58) Field of Classification Search
None
See application file for complete search history.

(56) References Cited

PUBLICATIONS

Chem. Eur. J., (2015), pp. 17570-17573.*
STN Registry database entry for CAS RN 72125-84-9, Entered STN Nov. 16, 1984, Accessed Sep. 3, 2018.*
"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
Wang et al., J. Immunol. 2007, 179, pp. 5958-5965.*

* cited by examiner

*Primary Examiner* — Alicia L Otton

(57) ABSTRACT

Disclosed herein are novel compounds of formula (I) and (II), each of which may serve as a reagent to deliver nitric oxide (NO) and a therapeutic agent to treat NO-associated diseases. Also disclosed are a pharmaceutical composition comprising the compound of formula (I) or (II), a composite material comprising the compound of formula (I) or (II), and the uses thereof.

2 Claims, 8 Drawing Sheets
(1 of 8 Drawing Sheet(s) Filed in Color)

DINITROSYL IRON COMPLEX, PHARMACEUTICAL COMPOSITION COMPRISING THE SAME, COMPOSITE MATERIAL COMPRISING THE SAME, AND USES THEREOF

BACKGROUND OF THE INVENTION

1. Field of the Invention

The present disclosure in general relates to the treatment of nitric oxide (NO)-related diseases. More particularly, the present disclosure relates to two types of dinitrosyl iron complex (DNIC), and their uses as a NO-releasing reagent to treat NO-associated diseases and/or conditions.

2. Description of Related Art

Nitric oxide (NO, also known as nitrogen oxide or nitrogen monoxide) has a formula of ●NO, in which the dot ● represents an unpaired electron on the nitrogen atom. ●NO involves a variety of signal transduction pathways in vascular, immune, and neuronal system in multicellular organisms, whereas the nature of ●NO and the location where ●NO is generated dictate its physiological and pathological function. ●NO interacts with the heme center of soluble guanylate cyclase (sGC) to promote the conversion of GTP into cGMP and to activate cGMP-dependent vascular relaxation of blood vessels, cGMP/MAPK-dependent angiogenesis, and cGMP-dependent release of neurotransmitter. Bacterial ●NO modulates hsf-1/daf-16 related genes to enhance stress resistance and longevity in C. elegans. Through the interaction with nuclear receptor proteins UNF and E75, ●NO provides a concentration-dependent switching mechanism between the neuronal degenerative and regenerative states of axon. In Alexander disease, a serious degenerative neurological disorder, ●NO derived from glia triggers astrocyte-mediated neuronal degeneration and cell death.

Nitroxyl ($NO^-$, also known as azanone) is a one-electron-reduction sibling of ●NO. Similar to ●NO, $NO^-$ has been shown to induce vasorelaxation via activating sGC. Besides, $NO^-$ also triggers a positive myocardial inotropic effect in the cardiovascular system that is independent from β-adrenergic signaling pathway, especially during a congestive heart failure condition. In addition to cardiovascular effects, it is reported that $NO^-$ exhibits an anti-cancer effect via inhibiting GAPDH activity.

Based on the biological functions, both ●NO and $NO^-$ donors have emerged as a promising agent to treat these ●NO and/or $NO^-$ related diseases. However, the current ●NO/$NO^-$ donors have some drawbacks, such as low activity, low solubility, poor specificity, short half-life, and adverse side-effect, that remain obstacles to clinical application. In view of the foregoing, there exists in the related art a need for a novel compound that has ●NO /$NO^-$ releasing activity and may be employed as a lead compound for preparing or manufacturing medicaments to treat ●NO/$NO^-$-associated diseases and conditions.

BRIEF SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a compound of formula (I),

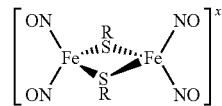

(I)

or its pharmaceutically acceptable salt, solvate, derivative or prodrug.

According to some embodiments of the present disclosure, R is $C_{1-6}$ alkyl or phenyl optionally substituted with —OH, —COON, or —$NH_2$; and x is an integral between −2 to +2. Suitable examples of R include, but are not limited to, —$CH_2CH_2OH$, —$CH_2CH_2COOH$, —$CH_2CH_3$, —$C_6H_5COOH$ and —$CH_2CH_2NH_2$. According to one preferred example, R is —$CH_2CH_2COOH$, and x is 0.

The second aspect of the present disclosure is directed to a compound of formula (II),

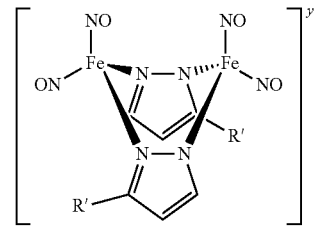

(II)

or its pharmaceutically acceptable salt, solvate, derivative or prodrug.

According to certain embodiments of the present disclosure, R' is —$NH_2$, —$NO_2$, —$CH_3$ or —$C_6H_5$, and y is an integral between −2 to +2. Preferably, R' is —$NH_2$, —$NO_2$ or —$C_6H_5$, and y is 0.

The present disclosure also provides a pharmaceutical composition and a composite material for delivery of NO so as to delay senescence, extend the lifespan, trigger the vasodilation, induce myocardial relaxation and inotropy, or treat a NO-associated disease and/or condition. The present pharmaceutical composition comprises, (a) an effective amount of the present compound of formula (I) or (II), its pharmaceutically acceptable salt, solvate, derivative or prodrug; and (b) a pharmaceutically acceptable excipient.

The present composite material comprises an active agent, and a metal-organic framework (MOF) having a pore structure for encapsulating the active agent therein, in which the active agent may be the compound of formula (I) or (II), its pharmaceutically acceptable salt, solvate, derivative or prodrug.

Another aspect of the present disclosure is directed to a method for delivery of NO in the purpose of delaying senescence, extending the lifespan, triggering the vasodilation, inducing myocardial relaxation and inotropy, or treating a NO-associated disease and/or condition. According to certain embodiments of the present disclosure, the method comprises administering to the subject in need thereof an effective amount of the pharmaceutical composition or the composite material in according to any aspects and embodiments of the present disclosure.

Exemplary diseases treatable by the present method include, but are not limited to, cardiovascular disease, diabetes mellitus, asthma, sickle cell disease, impotence, cystic fibrosis, pyloric stenosis, chronic kidney disease, neurodegenerative disorder, cancer, erectile dysfunction, and infectious disease.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE INVENTION

Figure 1:
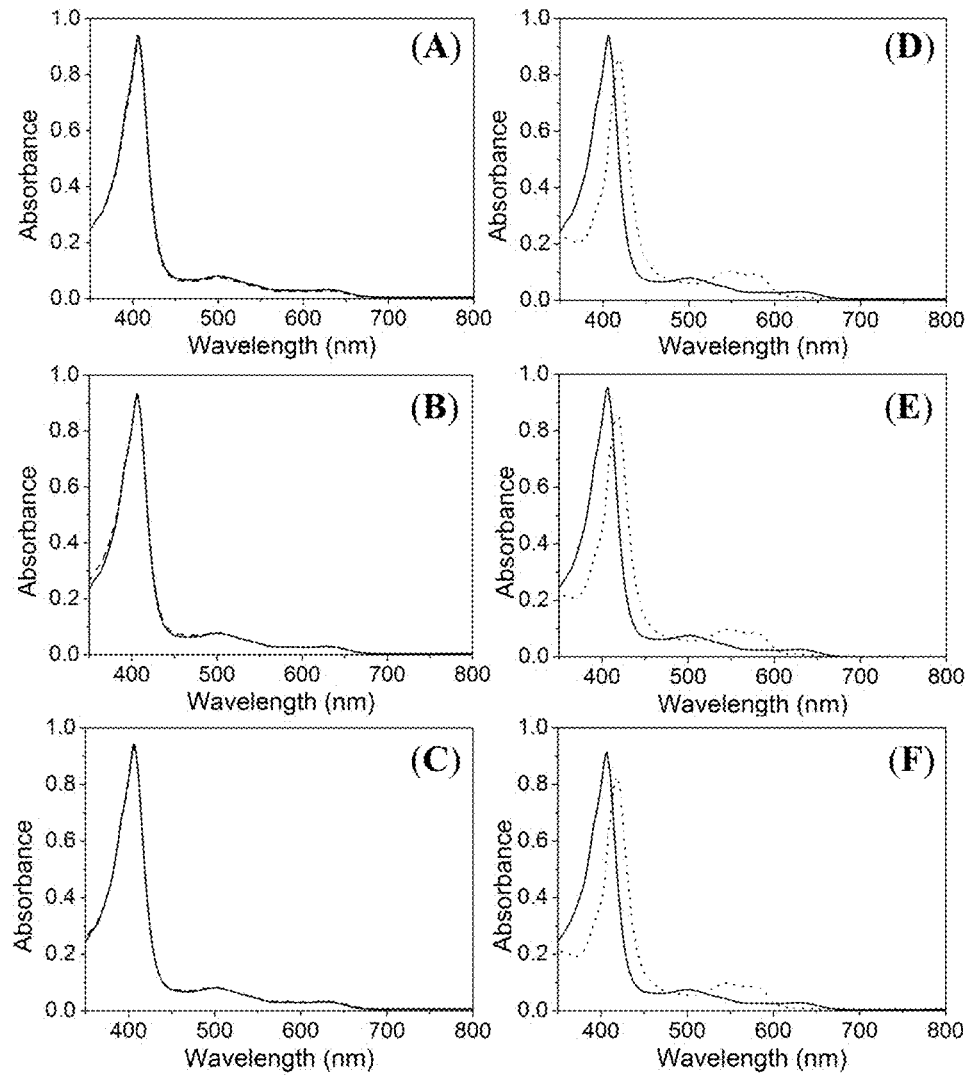
FIG. 1 are line charts that depict the UV-vis absorption of specified reactions according to Example 1 of the present disclosure; reaction of 10 μM metmyoglobin (metMb) with DNIC-1a (panel A), DNIC-1b (panel B), DNIC-1d (panel C), DNIC-2a (panel D), DNIC-2b (panel E), and DNIC-2d (panel F), respectively, in 25 mM phosphate buffer at pH 7.4 are monitored by UV-vis spectroscopy; the UV-vis spectra are measured after the reaction solution is incubated for 0 minute (solid line), 5 minutes (dotted line), and 8 hours (dashed line)

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, and $C_{3-4}$.

Unless otherwise indicated, the term "alkyl" means a straight chain, branched and/or cyclic ("cycloalkyl") hydrocarbon having from 1 to 6 (e.g., 1 to 6, 1 to 5, 1 to 4, 1 to 3, 1 to 2, or 1) carbon atoms. Alkyl moieties having from 1 to 4 carbons ($C_{1-4}$ alkyl) are referred to as "lower alkyl." Examples of alkyl groups include methyl, ethyl, propyl, isopropyl, n-butyl, t-butyl, isobutyl, 2-isopropyl-3-methyl butyl, pentyl, pentan-2-yl, hexyl, and isohexyl. Cycloalkyl moieties examples include cyclopropyl, cyclobutyl, cyclopentyl, and cyclohexyl. Unless otherwise specified, each instance of an alkyl group is independently optionally substituted, i.e., unsubstituted (an "unsubstituted alkyl") or substituted (a "substituted alkyl") with one or more substituents.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —CHO, —COON, —NH$_2$, alkoxy, alkanoyloxy (e.g., —OAc), alkenyl, alkyl (e.g., methyl, ethyl, propyl, t-butyl), aryl, aryloxy, halo, or haloalkyl (e.g., —CCl$_3$, —CF$_3$, —C(CF$_3$)$_3$). In a particular embodiment, the term "substituted," when used to describe a chemical structure or moiety, refers to a derivative of that structure or moiety wherein one or more of its hydrogen atoms is substituted with one or more of: hydroxyl, amino, or carboxyl.

Unless otherwise indicated, one or more adjectives immediately preceding a series of nouns is to be construed as applying to each of the nouns. For example, the phrase "optionally substituted alky or phenyl" has the same meaning as "optionally substituted alky, or optionally substituted phenyl."

As used herein, the term "nitric oxide" or "NO" refers to the reactive forms of nitric oxide, in particular (1) uncharged nitric oxide (having the formula of ●NO), (2) negatively charged nitric oxide (e.g., nitroxyl, which has the formula of NO$^-$), and (3) positively charged nitric oxide (e.g., nitrosonium, which has the formula of NO$^+$).

The term "prodrug" as used herein, refers to any compound that when administered to a biological system yields the "drug" substance either as a result of spontaneous chemical reaction(s) or by enzyme catalyzed or metabolic reaction(s).

The term "treating" encompasses partially or completely preventing, ameliorating, mitigating and/or managing a symptom, a secondary disorder or a condition associated with NO, in which increasing the level of NO provides a benefit to the subject having or suspected of having such symptom, disorder or condition. The term "treating" as used herein refers to application or administration of one or more compounds of the present disclosure to a subject, who has a symptom, a secondary disorder or a condition associated with NO, with the purpose to partially or completely alleviate, ameliorate, relieve, delay onset of, inhibit progression of, reduce severity of, and/or reduce incidence of one or more symptoms, secondary disorders or features associated with NO. Symptoms, secondary disorders, and/or conditions associated with NO include, but are not limited to, cardiovascular disease, diabetes mellitus, asthma, sickle cell disease, impotence, cystic fibrosis, pyloric stenosis, chronic kidney disease, neurodegenerative disorder, cancer, erectile dysfunction, and infectious disease. Treatment may be administered to a subject who exhibits only early signs of such symptoms, disorder, and/or condition for the purpose of decreasing the risk of developing the symptoms, secondary disorders, and/or conditions associated with NO. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the compound of the present disclosure), such as molar concentration, mass concentration, volume concentration, molality, mole fraction, mass fraction and mixing ratio. Specifically, the term "therapeutically effective amount" used in connection with the compound described herein refers to the quantity of compound, which is sufficient to alleviate or ameliorate the symptoms associated with the NO-associated disease in the subject. Persons having ordinary skills could calculate the human equivalent dose (HED) for the medicament (such as the present compound) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to an animal including the human species that is treatable with the compounds of the present disclosure. The term "subject" is intended to refer to both the male and female gender unless one gender is specifically indicated, and may be any age, e.g., a child or adult.

The present disclosure provides two types of compounds, each of which may serve as a NO-releasing agent so as to delay senescence, extend the lifespan, trigger the vasodilation, induce myocardial relaxation and inotropy, or treat a NO-associated disease and/or condition. The said NO comprises uncharged nitric oxide (●NO) and charged nitric oxide species, particularly including nitroxyl (NO⁻) and nitrosonium (NO⁺). The first type of compound has the structure of formula (I):

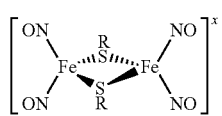

wherein R is $C_{1-6}$ alkyl or phenyl optionally substituted with —OH, —COON, or —NH$_2$, and x is an integral between −2 to +2.

According to embodiments of the present disclosure, R may be —CH$_2$CH$_2$OH, —CH$_2$CH$_2$COOH, —CH$_2$CH$_3$, —C$_6$H$_5$COOH or —CH$_2$CH$_2$NH$_2$. According to one example, R is —CH$_2$CH$_2$COOH, and x is 0.

According to one embodiment of the present disclosure, once administering to a subject, the first compound delays the aging process and prolongs the lifespan of the subject. According to another embodiment of the present disclosure, the first compound induces vasodilation and myocardial relaxation in the subject.

The second compound has the structure of formula (II):

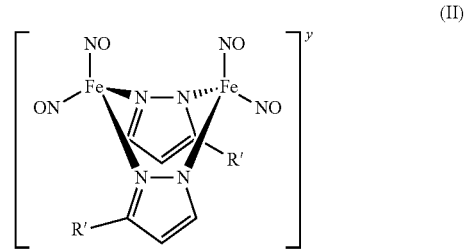

wherein R' is —NH$_2$, —NO$_2$, —CH$_3$ or —C$_6$H$_5$, and y is an integral between −2 to +2. According to the preferred embodiment, R' is —NH$_2$, —NO$_2$ or —C$_6$H$_5$, and y is 0.

According to one embodiment of the present disclosure, after administering to a subject, the second compound exhibits a myocardial inotropic effect therein; according to the embodiment, the second compound enhances the fractional shortening (FS) and cardiac output of the subject. According to another embodiment of the present disclosure, the second compound induces vasodilation in the subject.

Additionally, salts, solvates, derivatives and prodrugs of the compounds of formula (I) or (II) also are included in the present disclosure and can be used in the pharmaceutical composition, composite material and/or methods disclosed herein. The present disclosure further includes all possible stereoisomers and geometric isomers of the compounds of formula (I) or (II). The present invention includes both racemic compounds and optically active isomers. When a compound of formula (I) or (II) is desired as a single enantiomer, it can be obtained either by resolution of the final product or by stereospecific synthesis from either isomerically pure starting material or use of a chiral auxiliary reagent. Resolution of the final product, an intermediate, or a starting material can be achieved by any suitable method known in the art. Additionally, in situations where tautomers of the compounds of formula (I) or (II) are possible, the present disclosure is intended to include all tautomeric forms of the compounds. Prodrugs of compounds of formula (I) or (II) also are included in the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound. Suitable prodrugs include, for example, acid derivatives, such as amides and esters.

Salts of compounds of formula (I) or (II) can be prepared during the final isolation and purification of the compounds or separately by reacting the compound with an acid having a suitable cation. The pharmaceutically acceptable salts of compounds of formula (I) or (II) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Non-limiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of formula (I) or (II) appeared herein is intended to include compounds of formula (I) or (II) as well as pharmaceutically acceptable salts, solvates, or prodrugs thereof.

The compounds (I) and (II) may serve as a platform for delivery of NO, hence are potential lead compounds for manufacturing a medicament for treating a NO-associated disease or condition. Applicable disease or condition includes, but is not limited to, cardiovascular disease, diabetes mellitus, asthma, sickle cell disease, impotence, cystic fibrosis, pyloric stenosis, chronic kidney disease, neurodegenerative disorder, cancer, erectile dysfunction and infectious disease.

The second aspect of the present disclosure is directed to a pharmaceutical composition comprising an effective amount of an active agent and a pharmaceutically acceptable excipient. According to some embodiments of the present disclosure, the active agent is the compound of formula (I), or the pharmaceutically acceptable salt, solvate, derivative or prodrug thereof. According to certain embodiments of the present disclosure, the active agent is the compound of formula (II), or the pharmaceutically acceptable salt, solvate, derivative or prodrug thereof.

Depending on the desired purpose, the present pharmaceutical composition may be formulated into solid, semi-solid, or liquid forms, such as tablets, capsules, powders, granules, ointments, solutions, suppositories, and injections. As such, administration of the active compound can be achieved in various ways, including oral, enteral, nasal, topical, transmucosal, subcutaneous, intradermal, intramuscular, intravenous and intraperitoneal administration. In pharmaceutical dosage forms, the active compound may be administered alone or in combination with other known pharmaceutically active agent to treat NO-associated diseases and conditions. One of skilled person in the art is familiar with the various dosage forms that are suitable for use in each route. It is to be noted that the most suitable route in any given case would depend on the nature or severity of the disease or condition being treated.

In some embodiments, the present pharmaceutical compositions are solid dosage forms for oral administration. Such solid dosage forms may be capsules, sachets, tablets, pills, lozengens, powders or granules. In such forms, the active ingredient such as any of the compounds described above is mixed with at least one pharmaceutically acceptable excipient. Any of the described solid dosage forms may optionally contain coatings and shells, such as enteric coatings, and coatings for modifying the release rate of any of the ingredients. Examples of such coatings are well known in the art. In one example, the pharmaceutical compositions of this disclosure are tablets such as quick-release tablets. In still another example, the pharmaceutical compositions of this disclosure are formulated into sustained release forms.

In another example, the pharmaceutical compositions of this disclosure are powders that are encapsulated in soft and hard gelatin capsules.

In some embodiments, the present pharmaceutical compositions are liquid dosage forms for oral administration. The liquid formulation may further include a buffering agent to maintain a desired pH. The liquid dosage formulations may also be filled into soft gelatin capsules. For example, the liquid may include a solution, suspension, emulsion, microemulsion, precipitate or any desired liquid media carrying any of the compound as described above, or a pharmaceutically acceptable derivative, salt or solvate thereof, or a combination thereof. The liquid may be designed to improve the solubility of active compound as described above to form a drug-containing emulsion or disperse phase upon release.

In some embodiments, the pharmaceutical compositions of this disclosure are formulations suitable for parenteral administration, such as subcutaneous, intradermal, intramuscular, intraperitoneal and intravenous injection. The pharmaceutical compositions may be formulated as isotonic suspensions, solutions or emulsions in oily or aqueous vehicles, and may contain formulatoary agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

The third aspect of the present disclosure pertains to a composite material comprising an active agent, and a metal-organic framework (MOF) having a pore structure for encapsulating the active agent therein. According to some embodiments of the present disclosure, the active agent is the compound of formula (I), or the pharmaceutically acceptable salt, solvate, derivative or prodrug thereof. According to certain embodiments of the present disclosure, the active agent is the compound of formula (II), or the pharmaceutically acceptable salt, solvate, derivative or prodrug thereof.

In structure, MOF is a compound consisting of metal ions/clusters and organic ligands, in which the organic ligands server as linkers to link the metal ions/clusters. The thus forming network may have a one-, two-, or three-dimensional structure, and comprises a plurality of voids (such as pores and channels) therein. MOF serves as a promising platform for drug delivery, based on the advantages of high drug loadings, biodegradability and versatile functionality. The nature of MOF (e.g., the size or structure of MOF, and the number and shape of voids comprised therein) may vary with the type of metal ion, which is usually selected from the group consisting of, aluminum (Al), chromium (Cr), antimony (Sb), gallium (Ga), cobalt (Co), nickel (Ni), magnesium (Mg), manganese (Mn), iron (Fe), zinc (Zn), cadmium (Cd) and ruthenium (Ru). According to one embodiment of the present disclosure, the metal ion of the present MOF is Fe.

Then, an active agent (such as a therapeutic drug or the present compound) can be loaded into the voids of MOF by impregnation of MOF in a solution comprising the active agent. Upon exposure to a suitable nucleophile (for example, water, blood, protein, or enzyme) or a stimulation (for example, a temperature higher than room temperature (e.g., 37° C.) or an electromagnetic radiation (e.g., ultraviolet light)), the active agent is displaced from the MOF and released into the aqueous environment. According to one embodiment of the present disclosure, the present composite material is produced by incubation of the MOF MIL-88B (Fe) in the solution of the compound of formula (I).

Depending on the desired purpose, the present composite material can be produced by impregnating the MOF with different active agents, for example, the present compound (i.e., the compound of formula (I) or (II)) and an additional agent. The additional agent may be a targeting molecule (such as an antibody, an aptamer or a polypeptide exhibiting binding affinity to a tissue-specific antigen), a therapeutic drug, a prophylactic drug, or any agent that possesses some beneficial effects on delaying senescence or on treating NO-associated disease.

Another aspect of the present disclosure pertains to a method for delivery of NO in the purpose of delaying senescence, extending the lifespan, triggering the vasodilation, inducing myocardial relaxation and inotropy, or treating a NO-associated disease and/or condition in a subject. The method comprises administering to the subject an effective amount of a compound of formula (I) or (II). According to embodiments of the present disclosure, the NO released from the compound of formula (I) or (II) activates NO relevant signal pathway, which then induces an anti-aging response and/or a therapeutic effect in the subject. The methods of the present invention can be accomplished by administering a compound of formula (I) or (II) as the neat compound, as a pharmaceutical composition, or as a composite material.

Exemplary diseases treatable by the present method include, but are not limited to, cardiovascular disease, diabetes mellitus, asthma, sickle cell disease, impotence, cystic fibrosis, pyloric stenosis, chronic kidney disease, neurodegenerative disorder, cancer, erectile dysfunction, or infectious disease.

As would be appreciated, the present method can be applied to the subject, alone or in combination with additional treatment that have some beneficial effects on delaying senescence or on treating NO-associated disease. Depending on the therapeutic purpose, the present method can be applied to the subject before, during, or after the administration of the additional treatment.

The subject treatable by the present method may be a human or a non-human, for example, a worm, a fish, a mouse, a rat, a cat, a dog, a monkey, a chimpanzee, a sheep or a cow.

The compound of formula (I) or (II) can be administered to the subject via a route selected from the group consisting of oral, enteral, nasal, topical, transmucosal, and parenteral administration, in which the parenteral administration is any of subcutaneous, intradermal, intramuscular, intraarticular, intravenous, intraspinal, or intraperitoneal injection. According to some embodiments of the present disclosure, the compound of formula (I) or (II) is orally administered to the subject.

In one embodiment of the present disclosure, administration of the compound of formula (I) delays the aging process, and prolongs the lifespan of the subject. In another embodiment of the present disclosure, administration of the compound of formula (I) or (II) induces vasodilation. In still another embodiment of the present disclosure, administration of the compound of formula (I) induces myocardial relaxation. In still another embodiment of the present disclosure, administration of the compound of formula (II) induces myocardial inotropy. In further embodiment of the present disclosure, administration of the compound of formula (II) enhances fractional shortening (FS) and cardiac output.

As would be appreciated, the compound of formula (I) or (II) may be administered in combination with a targeting molecules (e.g., conjugated with the targeting molecule, or encapsulated in a vesicle having the targeting molecule linked therewith) so as to improve the therapeutic effect thereof. In general, the target molecule may be an antibody, an aptamer or a polypeptide exhibiting binding affinity to a tissue-specific antigen.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Instruments
The reagents metmyoglobin (TCl), Griess reagent (Aldrich), 5-bromo-4-chloro-3-indoyl-b-D-galactopyranoside (Aldrich), potassium ferrocyanide (Alfa Aesar), potassium ferriccyanide (ACROS), sodium nitroprusside (ACROS), epinephrine (Sigma) were used as received. De-ionized water was produced from Milli-Q reagent water purification system. Infrared spectra of the $v_{No}$ stretching frequencies were recorded on a JASCO 4200 spectrometer with sealed solution cells (0.1 mm, $CaF_2$ windows). UV-vis spectra were recorded on a JASCO V-630 spectrometer. Fluorescence spectra were recorded on a Hitachi F-7000 fluorescence spectrophotometer. Bright-field and fluorescence images were recorded under confocal microscope system (TCS-SP5-XAOBS, Leica, Germany; ECLIPSE TE2000-U, Nikon, Japan) and fluorescence microscope (SMZ1500, Nikon/HG Lamp MODEL LH-M100C-1/4000R, Qlamging).

Preparation of DNIC
$[(NO)_2Fe(\mu\text{-SEtOH})_2Fe(NO)_2]$ (DNIC-1a), $[(NO)_2Fe(\mu\text{-SEtCOOH})_2Fe(NO)_2]$ (DNIC-1b), $[(NO)_2Fe(\mu\text{-SEt})_2Fe(NO)_2]$ (DNIC-1c), $[(NO)_2Fe(\mu\text{-SPhCOOH})_2Fe(NO)_2]$ (DNIC-1d), and $[(NO)_2Fe(\mu\text{-SEtNH}_2)_2Fe(NO)_2]$ (DNIC-1e)

A THF solution of $[Fe(CO)_2(NO)_2]$ (1.0 mmol), freshly generated by reaction of [Na-18-crown-6-ether][Fe(CO)₃(NO)] (0.914g, 2 mmol) and [NO][$BF_4$] (0.256g, 2.2 mmol), was transferred via cannula under positive $N_2$ to a 20-mL Schlenk tube in which 4-mercaptobenzoic acid (0.2313 g, 1.5 mmol) was loaded. The reaction solution was stirred at ambient temperature for overnight, and then monitored by Fourier transform infrared spectroscopy (FTIR). The IR $v_{NO}$ and $v_{CO}$ spectrum showed three absorption peaks at 1787, 1759, 1720 $cm^{-1}$ and indicates the formation of complex $[(NO)_2Fe(\mu\text{-SPhCOOH})_2Fe(NO)_2]$ (DNIC-1d). This THF solution of DNIC-1d was then filtered through Celite. Addition of hexane to this THF solution of DNIC-1d led to the precipitation of brown solid of $[(NO)_2Fe(\mu\text{-SPhCOOH})_2Fe(NO)_2]$ (DNIC-1d) (yield 0.137 g, 23%). IR $v_{NO}$: 1787, 1759, 1720 $cm^{-1}$ (THF). Absorption spectrum (THF): 396 (10200) nm.

DNIC-1a (yield 0.102 g, 53%), DNIC-1b (yield 0.143 g, 81%), DNIC-1c (yield 0.103 g, 58%) and DNIC-1e (yield 0.110 g, 57%) were synthesized in a similar fashion. DNIC-1a: IR $v_{NO}$: 1779, 1752 $cm^{-1}$ (THF). Absorption spectrum ($H_2O$): 312 (9300), 362 (8500) nm. DNIC-1b: IR $v_{NO}$: 1776, 1751 $cm^{-1}$ (THF). Absorption spectrum ($H_2O$): 311 (9950), 362 (9100) nm. DNIC-1c: IR $v_{NO}$: 1773 (9800), 1748 (9000) cm$^{-1}$ (THF). Absorption spectrum (DMSO): 306, 361 nm. DNIC-1e: IR $v_{NO}$: 1773, 1748 cm$^{-1}$ (THF).

$[(NO)_2Fe(\mu-^{NH2}Pyr)_2Fe(NO)_2]$ (DNIC-2a), $[(NO)_2Fe(\mu-^{NO2}Pyr)_2Fe(NO)_2]$ (DNIC-2b), $[(NO)_2Fe(\mu-^{Me}Pyr)_2Fe(NO)_2]$ (DNIC-2c), and $[(NO)_2Fe(\mu-^{Pyr})_2Fe(NO)_2]$ (DNIC-2d)

$[Fe(CO)_2(NO)_2]$ (1.0 mmol) was freshly prepared by reaction of [Na-18-crown-6-ether][Fe(CO)$_3$(NO)] (0.446 g, 1.0 mmol) and [NO][BF$_4$] (0.116 g, 1.0 mmol) in THF at 4° C. This THF solution of $[Fe(CO)_2(NO)_2]$ (1.0 mmol) was then transferred via cannula under positive N$_2$ to a 20-mL Schlenk tube loaded with 3-aminopyrazolate (0.082 g, 1.0 mmol). After the reaction solution was stirred at ambient temperature for overnight, appearance of IR $v_{NO}$ peaks at 1807, 1790, 1736, and 1722 cm$^{-1}$ indicated the formation of complex $[(NO)_2Fe(\mu-^{NH2}Pyr)_2Fe(NO)_2]$ (DNIC-2a). Solvent was then removed under vacuum. The crude brown solid was redissolved in diethyl ether and then filtered through Celite. Solvent was then removed under vacuum to yield the dark-brown powder of $[(NO)_2Fe(\mu-^{NH2}Pyr)_2Fe(NO)_2]$ (DNIC-2a) (yield 0.182 g, 46%). IR $v_{NO}$: 1807, 1791, 1736, and 1722 cm$^{-1}$ (CH$_2$Cl$_2$); 1802, 1785, 1735, 1720 cm$^{-1}$ (diethyl ether). Absorption spectrum (CH$_3$OH): 339(3835).

DNIC-2b (yield 0.133 g, 67%), DNIC-2c (yield 0.124 g, 62%) and DNIC-2d (yield 0.148 g, 57%) were synthesized in a similar fashion. DNIC-2b: IR $v_{NO}$: 1813 sh, 1797 s, 1743 sh, 1728 s cm$^{-1}$ (THF); 1813 sh, 1802 s, 1745 s, 1737 sh (diethyl ether). Absorption spectrum (THF): 330(6900). DNIC-2c: IR $v_{NO}$: 1807 sh, 1793 s, 1739 sh, 1724 s cm$^{-1}$ (THF); 1809 sh, 1795 s, 1740 s, 1726 sh (CH$_2$Cl$_2$). Absorption spectrum (THF): 357(5870). DNIC-2d: IR $v_{NO}$: 1810, 1797, 1743, 1728 cm$^{-1}$ (THF); 1810, 1797, 1743, 1728 cm$^{-1}$ (CH$_2$Cl$_2$); 1811, 1798, 1746, 1731 cm$^{-1}$ (diethyl ether); 1810, 1801, 1745, 1736 cm$^{-1}$ (hexane). Absorption spectrum (THF): 323 (3900).

$[(NO)_2Fe(\mu-SEtCOOH)_2Fe(NO)_2]$@MIL-88B (Fe)

To a 20-mL Schlenk flask loaded with 0.1 g of MIL-88B (Fe) was added 5-mL THF solution of DNIC-1b (0.044 g, 0.1 mmol). The reaction solution was stirred at ambient temperature under N$_2$ atmosphere for 24 hours. The reaction solution was then centrifuged at 6000 rpm for 10 min before the above THF solution was removed. The residual brown solid was extracted with 5 mL of THF two times and then dried under vacuum (0.088 g). The IR spectrum of the brown solid exhibited two IR $v_{NO}$ stretching frequencies at 1777 and 1751 cm$^{-1}$, whereas the pXRD spectrum of the brown solid showed two strong peaks at 2θ=9.3° and 10.4°. These spectroscopic data demonstrated the successful synthesis of $[(NO)_2Fe(\mu-SEtCOOH)_2Fe(NO)_2]$@MIL-88B (Fe).

Crystallography

The crystals of DNIC-2b and DNIC-2d chosen for X-ray diffraction studies were mounted on a glass fiber and quickly coated in epoxy resin. Unit cell parameters were obtained by least-squares refinement. Diffraction measurement for DNIC-2b, and DNIC-2d was carried out on a SMART Apex CCD diffractometer with graphite-monochromated Mo K$_\alpha$ radiation (I=0.71073 A) and between 2.38 and 22.69° for DNIC-2b, between 1.59 and 25.04° for DNIC-2d, respectively. Least-squares refinement of the positional and anisotropic thermal parameters of all non-hydrogen atoms and fixed hydrogen atoms was based on F$^2$. A SADABS absorption correction was made. The SHELXTL structure refinement program was employed.

Reaction of $[(NO)_2Fe(\mu-^RPyr)_2Fe(NO)_2]$ (DNIC-2) and Metmyoglobin (metMb)

A typical procedure for nitroxyl-transfer reaction of DNIC-2 and metmyoglobin was described below using DNIC-2a as an example, whereas reaction of DNIC-2b/DNIC-2d and metMb follows the same procedure. 10 μM of metMb in 3.3 mL of 25 mM phosphate buffer (pH 7.4) was loaded in a 4-mL quartz cuvette and sealed with rubber septum under anaerobic N$_2$ atmosphere. 10 μM of DNIC-2a (13.0 μL of 2.5 mM stock solution of DNIC-2a in THF) was added into this aqueous solution, which is thermostated at 25° C. UV-vis spectra of this reaction solution were measured after this reaction solution was incubated for 10 minutes. Shift of UV-vis absorption bands from 407, 503 and 629 nm to 419, 543, and 577 nm indicated the nitroxyl transfer from DNIC-2a to metmyoglobin affording {Fe(NO)}$^7$ species (MbNO). DNIC-2b and DNIC-2d displayed similar nitroxyl-transfer reactivity toward metmyoglobin.

Reaction of $[(NO)_2Fe(\mu-SR)_2Fe(NO)_2]$ (DNIC-1) and Metmyoglobin (metMb)

A typical procedure for reaction of DNIC-1 and metmyoglobin was described below. To a 4-mL quartz cuvette containing 10 μM of metMb in 3.3 mL of 25 mM phosphate buffer (pH 7.4), 10 μM of DNIC-1, derived from 13.0 μL of 2.5 mM stock solution of DNIC-1 in THF was added via gas-tight syringe at room temperature. The reaction solution was incubated at ambient temperature for 8 hours. No change of UV-vis spectra for this reaction solution was observed.

In vitro release of ●NO from DNIC-1 characterized by Griess reagent and fluorescence probe FA-OMe A typical procedure for characterization of the total amount of nitric oxide released from DNIC-1a, DNIC-1b, and DNIC-1d using Griess reagent was described below. 15 μM DNIC-1 was prepared via addition of 300 μL of 0.75 mM stock solution of DNIC-1 in DMSO to 14.7 mL of 25 mM KPi buffer, pH 7.0. After this solution was incubated under aerobic condition for 48 hours, 1.5 mL of 10 mM Griess reagent in H$_2$O was added. A$_{540}$ was then measured to estimate the amount of nitric oxide released from DNIC-1 according to the calibration curve made of 0, 1, 2, 5, 10, 20, and 50 μM of NaNO$_2$, respectively. Three independent experiments were executed to measure the average amount of ●NO released from 15 μM of DNIC-1 a.

Release of nitric oxide from DNIC-1a, DNIC-1b, and DNIC-1d was also investigated using the fluorescence probe FA-OMe specific for ●NO. 20 μM FA-OMe was prepared via addition of 1.0 μL of 100 mM stock solution of FA-OMe in DMSO to 5 mL of 25 mM KPi buffer, pH 7.0. After addition of 500 μM DNIC-1 (50.0 μL of 50 mM stock solution of DNIC-1 in DMSO) to 20 μM FA-OMe, the fluorescence intensities were then recorded at 524 nm with excitation at 460 nm to corroborate the release of nitric oxide from DNIC-1 and DEANONOate, respectively.

Worm and Zebrafish Strains and Maintenance

All experiments were performed in accordance with animal protection standards and were approved by the Animal Investigation Committee of National Tsing Hua University (permit No. 00990001). WT C. elegans (N2) and CX3553 strain were obtained from C. elegans core facility Taiwan (CECF). Both strains were grown at 20° C. on nematode growth medium (NGM) plates with OP50 bacteria as food. AB (wild type) and Tg (kdr: EGFP) strains of zebrafish adults and embryos were used and maintained according to the guidelines described in the Zebrafish Book.

Uptake and Export of DNIC-1a in *C. elegans*

The uptake and export of DNIC-1a in *C. elegans* were evaluated based on the change of Fe content. 140 N2 worms were incubated with 500 μM of DNIC-1a for 15 minutes, washed with M9 buffer for three times, and transferred back to the agar plate containing *E. coli* OP50. These worms were then collected 0, 0.25, 0.5, 1, 2, and 6 hours later, respectively, and washed with M9 buffer for three times. Incubation of these worms with 80 μL household bleach and 25 μL of 10 M NaOH for 1 hour were then achieved to digest these worms. This solution was acidified via addition of 5% $HNO_3$ and diluted to 2.5 mL before the quantitation of Fe content by ICP-MS. Three independent experiments were conducted to measure the average values of Fe content in *C. elegans* after treatment of DNIC-1a. The background amount of Fe in the worms was measured in the similar fashion, except the exclusion of the step for incubation with 500 μM of DNIC-1a for 15 minutes.

In Vivo Release of ●NO from DNIC-1a in *C. elegans*

Ten N2 worms were incubated with 500 μM of DNIC-1a for 15 minutes and washed with M9 buffer for three times. After further incubation with 20 μM of FA-OMe for 0.5, 1, 2, and 4 hours, respectively, these worms were washed with M9 buffer for three times before the bright field and fluorescence images were taken. The fluorescence image was taken using the fluorescence microscope. For control experiments, N2 worms were incubated with either 500 μM of DNIC-1a for 15 minutes or 20 μM of FA-OMe for 30 minutes before the fluorescence images were taken.

Analysis of Lifespan in *C. elegans*

All experiments were executed at 20° C. and repeated at least three times. The worms at stage L4 were identified as day 0 for the analysis of lifespan. For the exposure of worms with DNIC-1a, worms were first moved to NGM plates without OP50 bacteria and then treated with 15 μM of DNIC-1a, prepared with M9 buffer, for 15 minutes on day 1, 4, and 7. Treatment steps for the control group were all the same, except that DNIC-1a was replaced with M9 buffer only. Worms were rinsed three times with M9 buffer after incubation and placed back to NGM plates with OP50 bacteria. Worms were considered dead when they stopped pharyngeal pumping or did not respond to pokes by a platinum wire. Worms died within seven days or with internal hatching were removed from the plates and excluded from lifespan calculation.

Analysis of Cell Senescence in *C. elegans*

Formation of cell senescence was evaluated based on the detection of senescence-associated beta-galactosidase (SA-βgal) activity using 5-bromo-4-chloro-3-indolyl-β-D-galactosiase (X-gal) as the substrate. All solutions and reagents used for β-Galactosidase cell staining were prepared according to the protocol. For the two treated groups, worms were transferred to NGM plates without OP50 bacteria. 10 μM of DNIC-1a and M9 buffer, respectively, were then provided on day 1, 4 and 7. Three-time wash with M9 buffer was executed after incubation. Worms were then placed back to NGM plates with OP50 bacteria and cultured until day 13. Worms on day 13 were collected and rinsed one time with 1× PBS before soaked with 1× fixative solution for 15 minutes. Worms were rinsed two times with 1× PBS after 1× fixative solution was removed. Worms were further incubated with the β-Galactosidase staining solution at 37° C. overnight. The intensity and area of the dark blue stain, which is indicative of SA-βgal activity, of each worm was quantified using ImageJ. All experiments were repeated at least three times. Control groups of worms on day 1, 7, and 13 were chosen individually for β-Galactosidase cell staining.

Activation of sGC in CX3553 Worms

The CX3553 (str-1::GFP) strain was selected to evaluate the activation of sGC using its intrinsic cGMP-dependent expression of GFP. 10 Worms on day 1 were treated with M9 buffer, 400 μM of DNIC-1a, and 400 μM of DNIC-2a, respectively, for 30 minutes and rinsed three times with M9 buffer. These worms were anesthetized via incubation with 0.1% tricane/0.01% tetramisole before the fluorescence images were taken. The fluorescence intensity of each worm was quantified using ImageJ.

Toxicity Test of DNIC in Zebrafish Embryos

WT-AB embryos at 3 days post fertilization (dpf) were soaked in 50 μM of DNIC-1a, 50 μM of DNIC-1b, 50 μM of DNIC-2a, and 200 μM of SNP for 30 minutes, respectively. The embryos were then rinsed three times and incubated at 28° C. The survival rate of embryos was tracked for the following 48 hours after the treatment. All experiments were triplicated.

Analysis of Vasodilation in Zebrafish Embryos

50 Tg (kdr:EGFP) embryos at 3 days post-fertilization (dpf) were incubated with fresh water, 50 μM of DNIC-1b, 50 μM of DNIC-2a, and 200 μM of sodium nitroprusside (SNP), respectively, for 30 minutes. The embryos were rinsed three times with fresh water after the treatment. Bright field and fluorescence images were then taken to measure the dorsal aorta diameter. All experiments were repeated three times.

Analysis of Myocardial Contractility and Cardiac Output in Zebrafish Embryos

Treatment of 3-dpf AB (wild type) embryos with fresh water, 50 μM of DNIC-1b, 50 μM of DNIC-2a, 200 μM of SNP, and 5 μg/mL epinephrine, respectively, for 30 minutes was conducted, which is followed by a three-time rinse with fresh water. 50 consecutive images recording at least 8 sequential cardiac cycles were taken to measure the short axis of the ventricular diameter during ventricular end systole (ES) and end diastole (ED). Fractional shortening was calculated from the formula:

$$FS = \frac{(D_d - D_s)}{D_d}.$$

Ventricular volume was calculated from the formula:

$$\text{Volume} = \left(\frac{4}{3}\right) \times \pi \times l \times s$$

assuming the ventricle as a prolate spheroid, whereas l is the long-axis radius and s is the short-axis radius of the ventricle. Heart rate, beats per minutes, was measured by counting the heart beats in 20 seconds manually. Cardiac output was calculated from the formula: cardiac output=heart rate×(ED volume−ES volume). All experiments were repeated at least three times.

Statistics

All data were analyzed using Microsoft Excel and displayed in means±SD. Data comparisons were made using Student's t-test or Log-Rank test. Differences were judged to be statistically significant at a p-value <0.05. Statistical significance was specialized as * for p-value <0.05,  for p-value <0.01, and * for p-value <0.001.

Example 1

Nitroxyl-transfer and NO-release Activities

In example 1, the reaction of a variety of DNICs with metmyoglobin was investigated so as to verify the universal role of bridging ligands, thiolate vs. pyrazolate, on dictating the NO⁻-transfer reactivity. As shown in FIG. 1, shift of the UV-vis absorption band from 407, 503, and 629 nm to 419, 543, and 577 nm upon addition of 10 µM DNIC-2 (FIG. 1, panels D-F) to 10 µM metmyoglobin, as opposed to the unreactive DNIC-1 (FIG. 1, panels A-C), supports the formation of MbNO and demonstrates the critical role of pyrazolate ligand on the rapid nitroxyl-transfer reactivity of DNIC-2.

Figure 2:
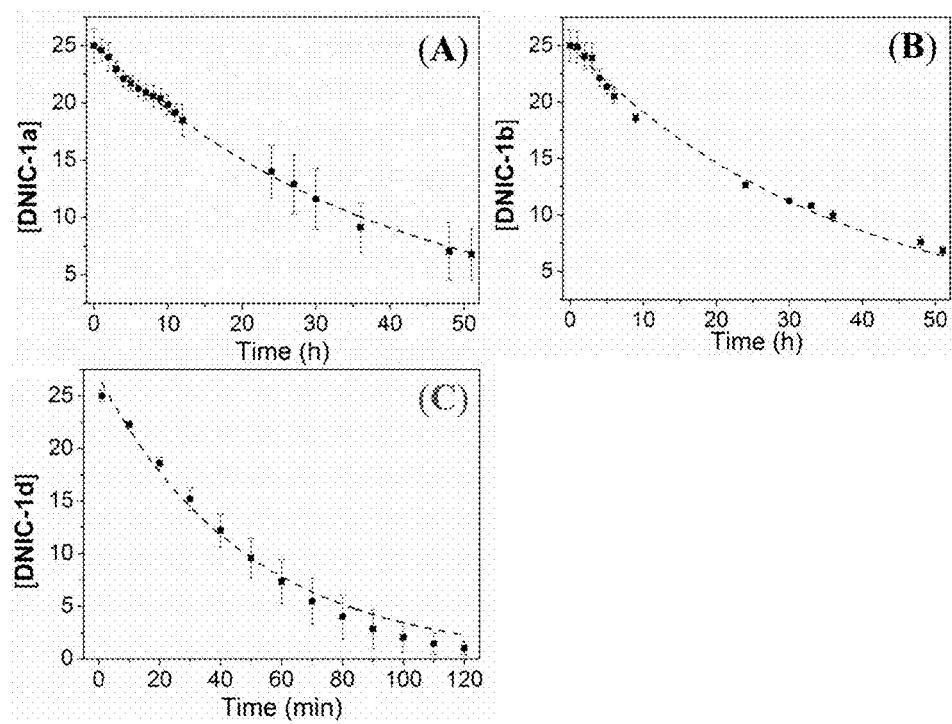
FIG. 2 are line charts that depict the UV-vis absorption of specified reactions according to Example 1 of the present disclosure; time-dependent decomposition of DNIC-1a (panel A), DNIC-1b (panel B), and DNIC-1d (panel C) in aerobic 25 mM KPi buffer, pH 7.0, are monitored by UV-vis spectroscopy; the absorbance at 362 nm, 361 nm or 396 nm is monitored by UV-vis spectroscopy to estimate the decomposition rate of DNIC-1a, DNIC-1b, and DNIC-1d, respectively.
Figure 3:
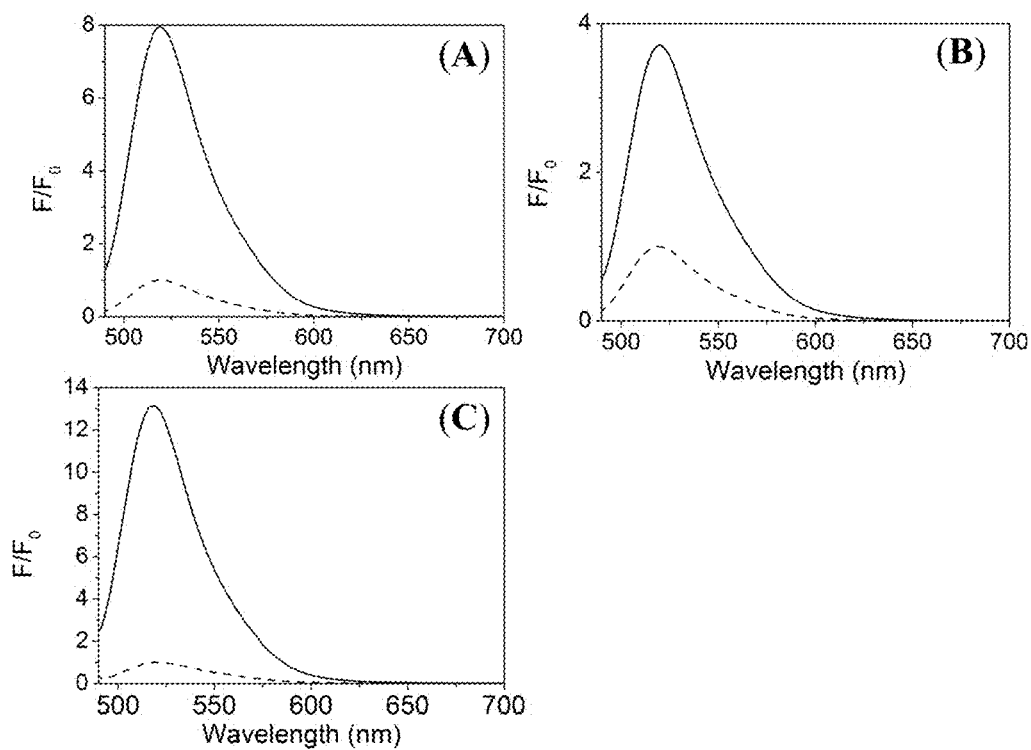
FIG. 3 are line charts that depict the UV-vis absorption of specified reactions according to Example 1 of the present disclosure; in vitro detection of nitric oxide released from DNIC-1a (panel A), DNIC-1b (panel B), and DNIC-1d (panel C) by use of 5-amino-2-(6-hydroxy-3-oxo-3H-xanthen-9-yl) benzoic acid methyl ester (FA-OMe); 500 μM of DNIC-1 is added to 10 μM of FA-OMe in 25 mM KPi buffer, pH 7.0; the fluorescence intensities are then detected with excitation at 460 nm after the reaction solution is incubated for 0 hour (dashed line) and 13 hours (solid line), respectively.

Regarding the reported ●NO electronic structure in DNIC-1c and the null NO⁻-transfer reactivity, the ●NO-release reactivity of DNIC-1 was evaluated by colorimetric Griess reagent and specific fluorescence probe FA-OMe. In contrast to the stability of DNIC-1a under anaerobic condition, steady decay of the UV-vis absorption band at 362 nm under aerobic condition revealed the $O_2$-triggered decomposition of DNIC-1a (FIG. 2). In addition, the half-life of DNIC-1a, DNIC-1b, and DNIC-1d are 27.4±0.5 hours, 25.9±0.4 hours, and 0.6±0.1 hour, respectively, assuming that the decay of DNIC-1 followed the pseudo-first order kinetics. As illustrated in Table 1 and FIG. 3, the colorimetric Griess reagent and specific fluorescence probe FA-OMe further corroborated that the aerobic decomposition of DNIC-1 is coupled with the steady release of ●NO. Based on the steady ●NO-release reactivity of DNIC-1 and distinctive NO⁻-transfer reactivity of DNIC-2, the dual ●NO/NO⁻-donor reactivity of DNIC-1/DNIC-2 in vivo and their biological activity on NO-responsive physiology were then accessed. DNIC-1a, DNIC-1b, and DNIC-2a were chosen for further in vivo study considering the solubility in aqueous solution.

TABLE 1

Total amount of NO released from DNIC-1 determined by Griess reagent

| DNIC-1a[a] | DNIC-1b[a] | DNIC-1d[a] |
|---|---|---|
| 30.3 ± 1.0 µM | 26.1 ± 0.1 µM | 24.4 ± 0.2 µM |

[a]The concentration of DNICs are 15 µM.

Example 2

Biological Function 2.1 Effect on Aging and Lifespan

Figure 4:
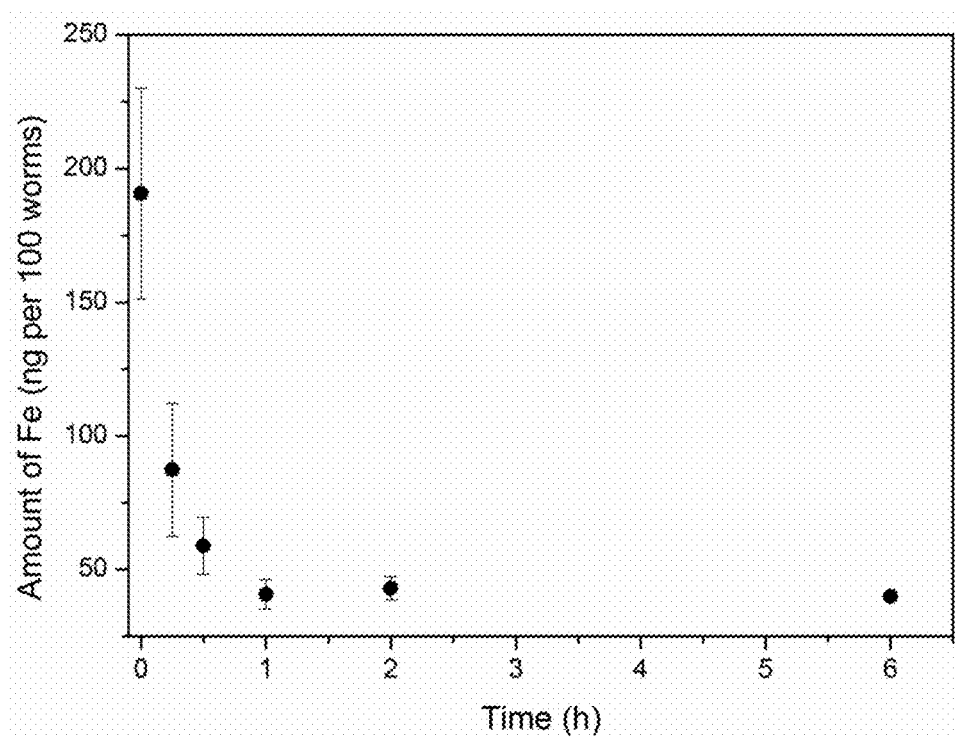
FIG. 4 is a dot plot that depicts the time-dependent change of iron (Fe) content in C. elegans incubated with DNIC-1a according to Example 2.1 of the present disclosure; 140 N2 worms are incubated with 500 μM of DNIC-1a for 15 minutes; these worms are then washed with M9 buffer for three times, digested under alkaline condition, and diluted to 2.5 mL; the Fe content, which is indicative for the uptake and export of DNIC-1a in C. elegans, is then measured by use of ICP-MS; average values of Fe content from three independent experiments are expressed as means±standard deviation; the amount of Fe in the worms without incubation with 500 μM of DNIC-1a is 46.8±3.6 ng per 100 worms.
Figure 5:
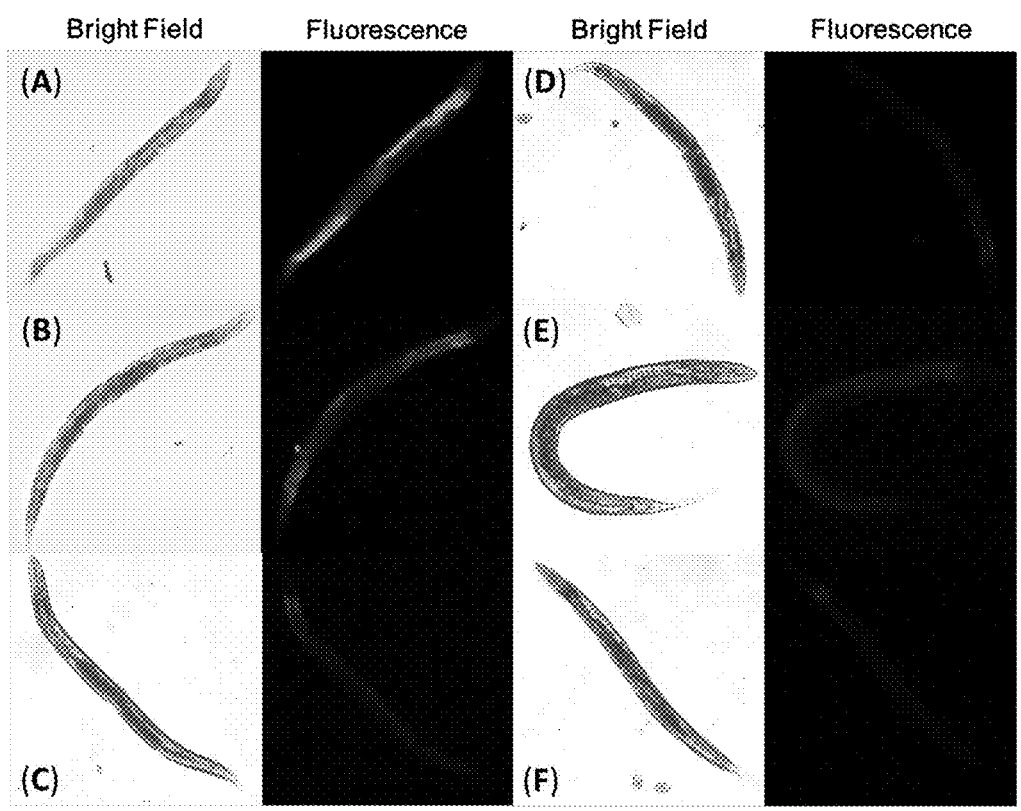
FIG. 5 are photographs depicting the detection of ●NO released from DNIC-1a in C. elegans by use of FA-OMe according to Example 2.1 of the present disclosure; N2 worms are incubated with 500 μM of DNIC-1a for 15 minutes and then washed with M9 buffer for three times; after further incubation with 10 μM of FA-OMe for 0.5 hour (panel A), 1 hour (panel B), 2 hours (panel C), and 4 hours (panel D), respectively, these worms are washed with M9 buffer for three times before the bright field and fluorescence images are taken; the bright field and fluorescence images of worms that are respectively incubated with 10 μM of FA-OMe for 0.5 hour (panel E) and 500 μM of DNIC-1a for 15 minutes (panel F)

Extensive study on the mechanism for aging process using the transparent and primitive *C. elegans* with short lifespan was pursued to identify the aging-related genes and biological active compounds for modulation of aging. Trafficking of DNIC-1a in *C. elegans* and, in the meanwhile, the function of released ●NO from DNIC-1a on the aging process were investigated in Example 2.1. FIG. 4 depicted the kinetic profile for the change of total amount of Fe in 140 N2 worms incubated with 500 µM of DNIC-1a for 15 minutes. Acute increase of total amount of Fe to 190.7±39.4 ng per 100 worms right after treatment of DNIC-1a, compared to the original 46.8±3.6 ng per 100 worms, followed by rapid attenuation of Fe content demonstrated the efficient uptake of DNIC-1a by *C. elegans* and rapid metabolism to export it (FIG. 4). ●NO-release reactivity of DNIC-1a during its trafficking in *C. elegans* was further evaluated using the specific fluorescence probe FA-OMe. Compared to the absence of fluorescence signal in *C. elegans* incubated with only FA-OMe or only DNIC-1a (FIG. 5, panels E and F), DNIC-1a released ●NO in the intestine of *C. elegans* (FIG. 5, panel A). Time-dependent decrease of ●NO release, according to the decreased fluorescence signal, resembled the kinetics for the trafficking of DNIC-1a in *C. elegans* (FIG. 5, panels A-D).

Figure 6:
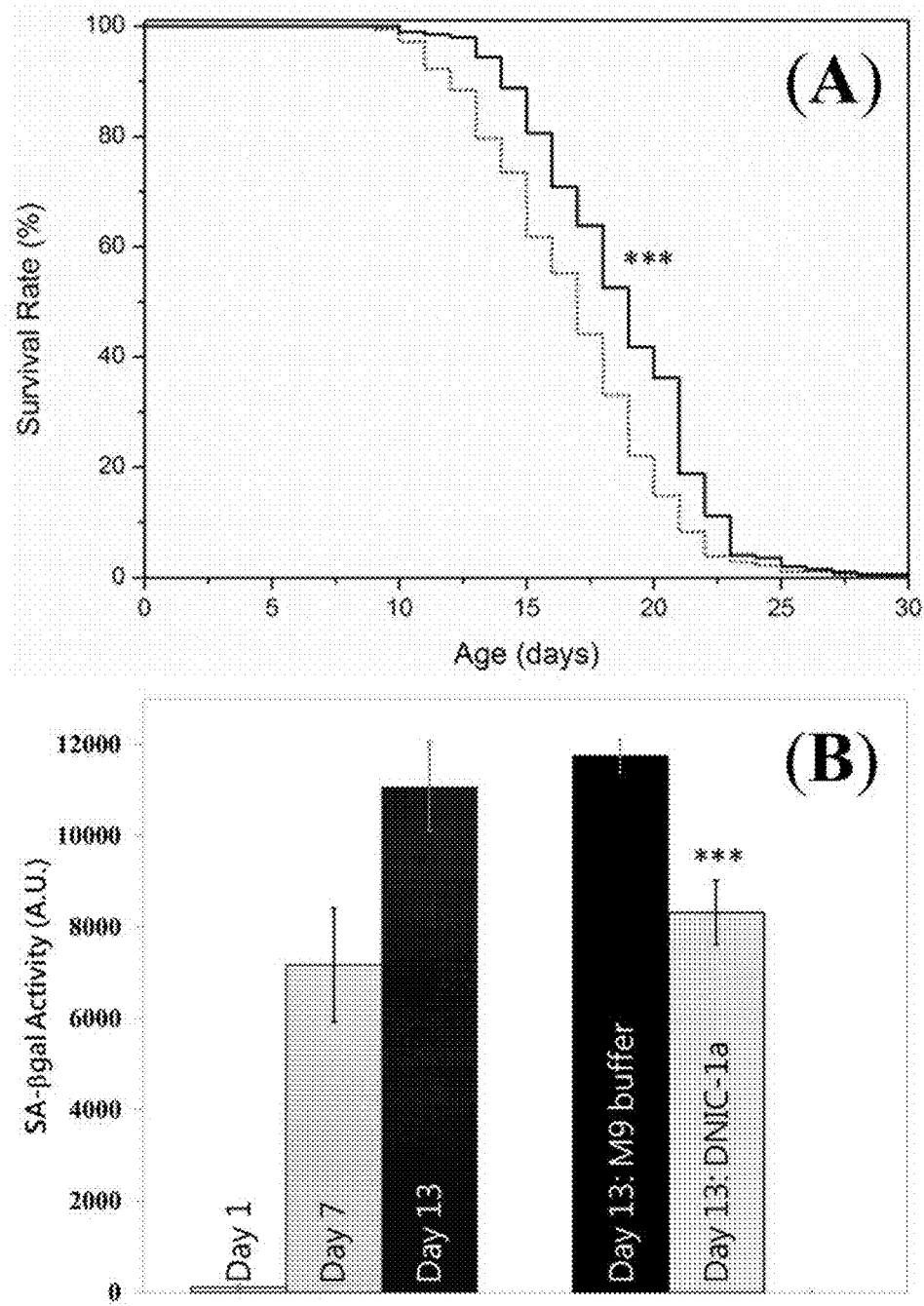
FIG. 6 are the data depicting the lifespan of C. elegans treated with or without the ●NO-donor DNIC-1a according to Example 2.1 of the present disclosure; panel A: on day 1, 4, and 7, N2 worms are respectively incubated with 0 μM (dotted line) and 10 μM of DNIC-1a (solid line) for 15 minutes, and then washed with M9 buffer for three times; average lifespan of C. elegans (n=200) from three independent experiments reveals the extension of the lifespan of C. elegans by DNIC-1; panel B: senescence-associated β-galactosidase activity (SA-β-gal activity) in C. elegans analyzed by chromogenic substrate X-gal; comparison of the SA-β-gal activity in 1-day-old, 7-day-old, 13-day-old worms reveals the aging-dependent accumulation of senescent cell; average values of SA-β-gal activity from three independent experiments are expressed as means±standard deviation; *P <0.05; P <0.01; *P <0.001.

To explore the biological function of ●NO released from DNIC-1a in *C. elegans*, influence of DNIC-1a on the lifespan and on the formation of cell senescence, which is indicative of biological aging, was further evaluated. Lifespan analysis on the *C. elegans* (n=200) respectively incubated with 0 µM and 10 µM of DNIC-1a for 15 minutes on Day 1, 4, and 7 was achieved. Tri-incubation of *C. elegans* with 10 µM of DNIC-1a resulted in a 10.7% extension of lifespan from 16.9±0.5 days to 18.7±0.4 days (FIG. 6, panel A). Accumulation of senescent cells during the biological aging process was reported to negatively influence lifespan and promote age-dependent changes in mice, whereas clearance of senescent cells delays aging-associated disorders. In order to reflect the ●NO-dependent extension of worm lifespan on the development of biological aging, senescence-associated β-galactosidase activity (SA-βgal) was assayed using chromogenic substrate 5-bromo-4-chloro-3-indoyl-β-D-galactopyranoside (X-gal) to characterize the formation of cell senescence and development of biological aging. In contrast to the aging-dependent accumulation of senescent cells, tri-incubation of *C. elegans* with 10 µM DNIC-1a for 15 minutes on Day 1, 4, and 7 significantly delayed the cell senescence (FIG. 6, panel B). Moreover, the comparable SA-βgal activity in 13-day-old worms treated with DNIC-1a and 7-day-old worms unveiled that DNIC-1a slowed down the aging process and extended the lifespan of *C. elegans*.

2.2 Effect on Vascular and Myocardial System

Figure 7:
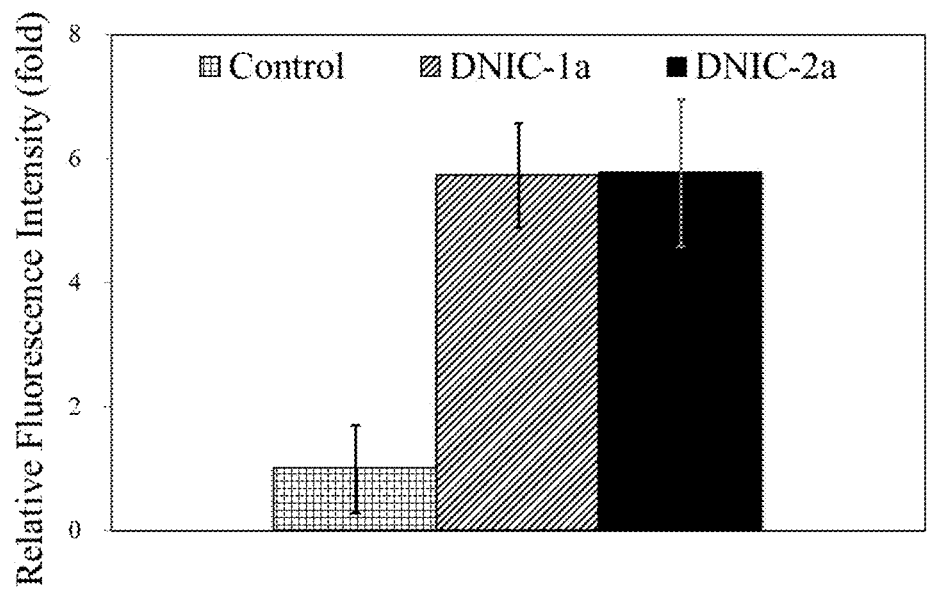
FIG. 7 is the data depicting the relative fluorescence intensity of worms treated with specified treatment according to Example 2.2 of the present disclosure; CX3553 (str-1::GFP) worms (n=10) are incubated with 400 μM of DNIC-1a (or 400 μM of DNIC-2a) for 30 minutes and then washed with M9 buffer for three times; these worms are anesthetized by 0.1% tricane/0.01% tetramisole before the fluorescence images are taken; quantitation of the fluorescence intensity depicts the activation of sGC by DNICs in CX3553 (str-1::GFP); average values of fluorescence intensity from three independent experiments are expressed as means±standard deviation; *P <0.05; P <0.01; *P <0.001.
Figure 8:
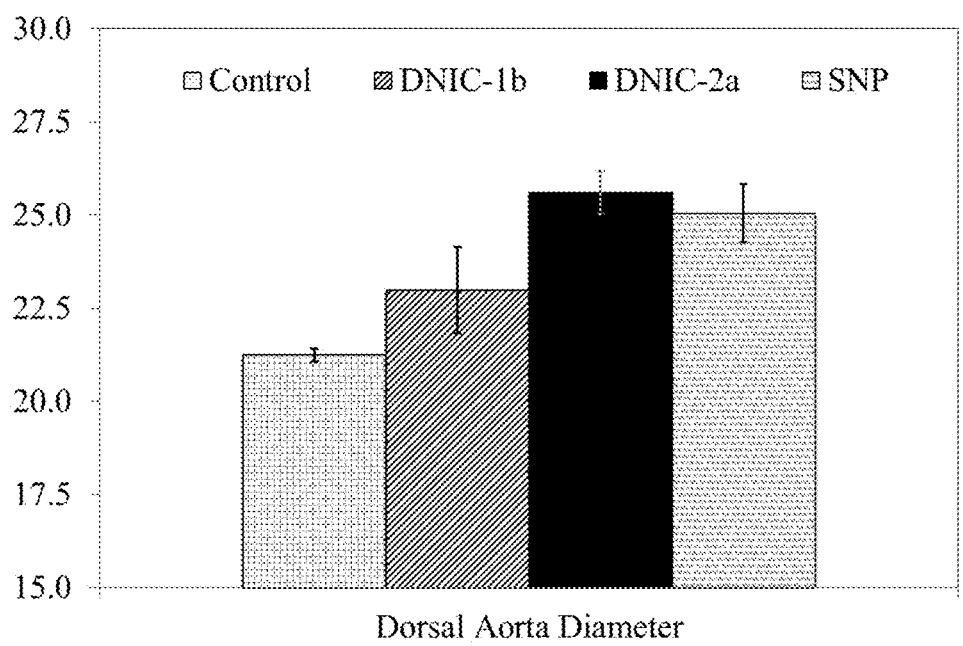
FIG. 8 is the data depicting the vasodilation effect of specified treatment according to Example 2.2 of the present disclosure; 3-day-old KDR zebrafish (n=50) is incubated with fresh water, 50 μM of DNIC-1b, 50 μM of DNIC-2a or 200 μM of sodium nitroprusside (SNP) for 30 minutes; after the fish is washed with fresh water for three times, bright field and fluorescence images are taken to measure the dorsal aorta diameter; vasodilation effect of DNIC-1b, DNIC-2a, and SNP on the diameter of dorsal aorta of zebrafish; average values of vessel diameter from three independent experiments are expressed as means±standard deviation that illustrates the vasodilation effect of ●NO-donor DNIC-1b and SNP as well as the NO$^-$-donor DNIC-2a; *P <0.05; P <0.01; *P <0.001.

In addition to the critical function of ●NO-release reactivity of DNIC-1a on long-term physiological regulation of aging process, the role of ●NO-release reactivity of DNIC-1a and efficient NO⁻-transfer reactivity of DNIC-2a in vascular and myocardial system was investigated. Soluble guanylate cyclase (sGC) was evolved to sense both ●NO and NO⁻ for accelerated conversion of GTP into cGMP and for ●NO/cGMP-dependent physiology. Using the heme-containing sGC in *C. elegans* as an in vivo sensor for NO, CX3553 worms featuring cGMP-dependent expression of green fluorescence protein (GFP) in AWB neurons were adopted to screen the nitrosylation reactivity of DNIC-1a and DNIC-2a. As illustrated in FIG. 7, both DNIC-1a and DNIC-2a resulted in about 5.7 fold increase of the GFP fluorescence signal in CX3553 worms. This turn-on demonstrated that the efficient nitrosylation reactivity of both DNIC-1a and DNIC-2a toward the $Fe^{II}/Fe^{III}$-heme center of sGC activated the transformation of GTP into cGMP. To project the NO-responsive activation of sGC on physiological activity in vascular system, zebrafish embryo, moreover, was utilized to assess the vasolation effect of DNICs. Sodium nitroprusside (SNP), a ●NO-donor approved for clinical usage, was adopted to contrast the efficacy of DNICs as a novel NO-donor. A initial toxicity test of DNIC-1a, DNIC-1b, and DNIC-2a was achieved through incubation of 3-dpf zebrafish with water, 50 µM DNIC-1a, 50 µM DNIC-1b, 50 µM DNIC-2a, and 200 µM SNP, respectively, for 30 minutes (Table 2). 50 µM DNIC-1b, 50 µM DNIC-2a, and 200 µM SNP displayed no acute toxicity on zebrafish embryo, while a dramatic death of 5-dpf zebrafish after treated with DNIC-1a on day 3 was observed. As a consequence, the effect of DNIC-1a on vasodilation and cardiac function is not reported. 3-dpf KDR zebrafish was incubated with fresh water, 50 µM DNIC-1b, 50 µM DNIC-2a, and 200 µM SNP, respectively, for 30 minutes. After the fish was washed with fresh water for three times, fluorescence images were taken to measure the dorsal aorta diameter. As shown in FIG. 8 and Table 3, the Fe-NO complexes DNIC-1b, DNIC-2a, and SNP initiated a vasodilation effect, presumably through the sGC/cGMP signaling pathway, to increase the diameter of dorsal aorta from 21.2±0.2 μm to 23.0±1.1 μm, 25.6±0.6 μm, and 25.1±0.8 μm, respectively.

TABLE 2

Survival rate of zebrafish incubated with Fe—NO complexes for 30 minutes on day 3 (n = 300, triplicated)

| Complex | Concentration | Day 3 | Day 4 | Day 5 |
|---|---|---|---|---|
| DNIC-1a | 50 μM | 100 ± 0.0% | 86.4 ± 10.5% | 62.3 ± 19.3% |
| DNIC-1b | 50 μM | 100 ± 0.0% | 100 ± 0.0% | 100 ± 0.0% |
| DNIC-2a | 50 μM | 100 ± 0.0% | 99.6 ± 0.7% | 98.4 ± 2.7% |
| SNP | 200 μM | 100 ± 0.0% | 100 ± 0.0% | 99.2 ± 1.4% |

TABLE 3

Short-axis diameter, fractional shortening, ventricular volume, dorsal aorta diameter, heart rate, and cardiac output of zebrafish with/without incubation of Fe—No complexes

| | | Control | DNIC-1b[a] | DNIC-2a[a] | SNP[a] | Epinephrine |
|---|---|---|---|---|---|---|
| Short Axis Diameter | ED($D_d$)[b] | 82.2 ± 2.0 | 92.3 ± 2.9 | 83.3 ± 2.5 | 86.4 ± 1.5 | 80.9 ± 1.4 |
| (μm) | ES($D_s$)[b] | 70.4 ± 2.5 | 72.3 ± 3.1 | 59.6 ± 1.7 | 71.5 ± 1.7 | 61.0 ± 2.5 |
| Fractional Shortening[c] | | 0.14 ± 0.02 | 0.22 ± 0.03 | 0.28 ± 0.02 | 0.26 ± 0.03 | 0.25 ± 0.04 |
| Ventricular Volume[d] | ED[b] | 0.55 ± 0.02 | 0.66 ± 0.05 | 0.55 ± 0.03 | 0.62 ± 0.06 | 0.46 ± 0.05 |
| (nL) | ES[b] | 0.33 ± 0.02 | 0.32 ± 0.05 | 0.21 ± 0.02 | 0.32 ± 0.01 | 0.20 ± 0.03 |
| | ED-ES | 0.21 ± 0.02 | 0.34 ± 0.05 | 0.34 ± 0.02 | 0.30 ± 0.06 | 0.26 ± 0.05 |
| Vessel Diameter (μm) | | 21.2 ± 0.2 | 23.0 ± 1.1 | 25.6 ± 0.6 | 25.1 ± 0.8 | — |
| Heart Rate (bpm) | | 124 ± 4 | 133 ± 5 | 145 ± 7 | 143 ± 5 | 144 ± 8 |
| Cardiac Output[e] (nL/min) | | 25.9 ± 4.5 | 45.8 ± 5.1 | 48.4 ± 4.5 | 42.8 ± 8.2 | 37.4 ± 6.1 |

[a]Zebrafish was incubated with 50 μM of DNIC-1b, 50 μM of DNIC-2a, 200 μM of SNP, and 5 μg/mL epinephrine, respectively, for 30 min and washed three times with fresh water before the measurement was executed.
[b]ED = end diastole, ES = end systole, $D_d$ = short axis diameter at end diastole, $D_s$ = short axis diameter at end systole.

[c]Fractional shortening was calculated from the formula $FS = \frac{(D_d - D_s)}{D_d}$.

[d]Ventricular volume was calculated from the formula $Volume = \left(\frac{4}{3}\right) \times \pi \times l \times s$ assuming the ventricle as a prolate spheroid, whereas l is the long-axis radius and s is the short-axis radius of the ventricle.

[e]Cardiac output was calculated from the formula: cardiac output = heart rate × (ED volume − ES volume).

2.3 Inotropic Effect

Figure 9:
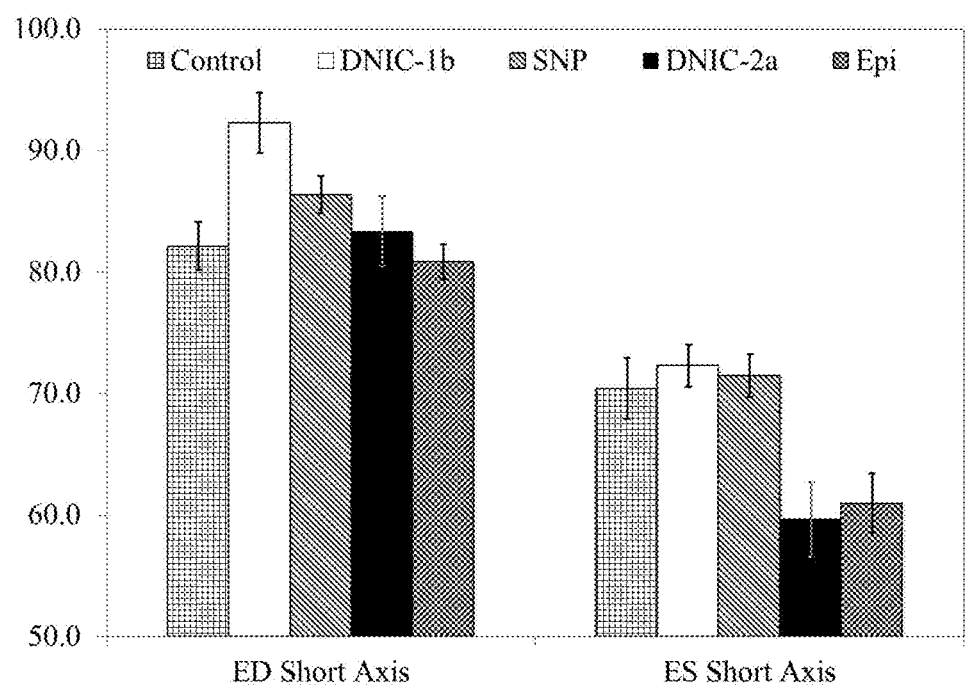
FIG. 9 is a histogram depicting the short-axis ventricular diameter of zebrafish during ED and ES; WT-AB zebrafishes (n=50) are respectively incubated with fresh water, 50 μM of DNIC-1b, 50 μM of DNIC-2a, and 200 μM of SNP for 30 minutes; after washing with fresh water for three times, 50 consecutive images recording at least 8 sequential cardiac cycles, with 25 ms exposure time, are taken to measure the short-axis ventricular diameter in WT-AB zebrafish heart during ventricular ES and ED; average values from three independent experiments are expressed as means±standard deviation; ●NO-donor DNIC-1b or SNP increases the short-axis ventricular diameter during ED, while NO$^-$-donor DNIC-2a elicits a myocardial inotropic effect to shorten the short-axis ventricular diameter and to reduce the ventricular

Observation of efficient nitroxyl-transfer reactivity of DNIC-2 toward $Fe^{III}$-heme center as well as the potent efficacy on activation of sGC for vasodilation inspired us to characterize its role in myocardial system using the transparent zebrafish embryo. DNIC-1b and SNP were utilized as a dedicated ●NO-donor to contrast the dual function of ●NO/NO⁻ in myocardial system, whereas epinephrine (epi) was used as a representative compound for activation of β-adrenergic dependent signaling pathway. After incubation of 3-dpf zebrafish with water, 50 μM DNIC-1b, 50 μM DNIC-2a, 200 μM SNP, and 5 pg/mL epi, respectively, for 30 minutes, 50 consecutive images of the heart area were taken to record 8 sequential cardiac cycles. Table 3 summarized the short-axis diameter at end diastole (ED) and end systole (ES), fractional shortening, ventricular volume, heart rate, and cardiac output. Of interest, a significant increase of the short-axis diameter of the heart and ventricular volume at end diastole (ED) was observed in the zebrafish treated with either DNIC-1b or SNP. This increase of ED short axis demonstrated that the ●NO-releasing Fe-NO complexes triggered the myocardial relaxation at ED, while no effect was observed at end systole (Table 3, FIG. 9). The NO⁻-donor DNIC-2a, in contrast, initiated a myocardial inotropic effect to enhance the myocardial contractility according to the significant decrease of the diameter of heart short-axis at end systole (ES). Among ●NO-donor DNIC-1b/SNP, NO⁻-donor DNIC-2a, and β-adrenergic dependent epinephrine, the most potent DNIC-2a triggered about 2-fold enhancement fractional shortening and cardiac output to strengthen the myocardial and cardiovascular function.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A compound of formula (II),

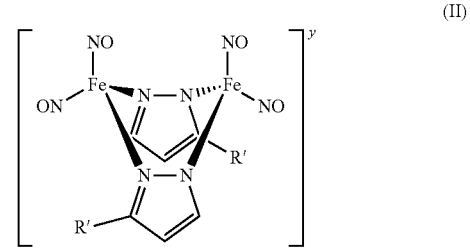

or its pharmaceutically acceptable salt or solvate, wherein,
R' is —$NH_2$, —$NO_2$, or —$C_6H_5$; and
y is an integer between −2 to +2.

2. The compound of claim 1, wherein R' is —$NH_2$, and y is 0.

* * * * *